(12) United States Patent
Vargas Munita et al.

(10) Patent No.: US 6,414,035 B1
(45) Date of Patent: Jul. 2, 2002

(54) USE OF POLYOLS IN COMBATING YEAST INFECTION AND POLYOL PREPARATIONS FOR SAID USE

(75) Inventors: Sergio Luis Vargas Munita, Santiago (CL); Julita Pearson, Kent (GB); Markku Virkki, Espoo (FI); Tammy Pepper, Weybridge; David Saunders, Farnham, both of (GB)

(73) Assignee: Xyrofin Oy, Kotka (FI)

( * ) Notice: Subject to any disclaimer, the term of this patent is extended or adjusted under 35 U.S.C. 154(b) by 0 days.

(21) Appl. No.: 09/555,581

(22) PCT Filed: Dec. 1, 1998

(86) PCT No.: PCT/FI98/00934

§ 371 (c)(1),
(2), (4) Date: Sep. 25, 2000

(87) PCT Pub. No.: WO99/27922

PCT Pub. Date: Jun. 10, 1999

(30) Foreign Application Priority Data

Dec. 1, 1997 (FI) .................................................. 974385

(51) Int. Cl.$^7$ ............................................ A61K 31/045
(52) U.S. Cl. ...................................................... 514/724
(58) Field of Search ................................... 514/53, 724

(56) References Cited

U.S. PATENT DOCUMENTS

| | | | |
|---|---|---|---|
| 3,422,184 A | 1/1969 | Goldman et al. | 424/48 |
| 4,514,422 A | 4/1985 | Yang et al. | 426/3 |
| 4,605,556 A | 8/1986 | Sato et al. | 424/85 |
| 4,725,440 A | 2/1988 | Ridgway et al. | 424/465 |
| 5,270,032 A | * 12/1993 | Pollock et al. | 424/49 |
| 5,431,915 A | 7/1995 | Harvey et al. | 424/439 |
| 5,482,053 A | 1/1996 | Kelly | 128/844 |
| 5,686,089 A | 11/1997 | Mitra et al. | 424/405 |
| 6,251,875 B1 | * 6/2001 | Saunders et al. | 514/53 |

FOREIGN PATENT DOCUMENTS

| | | |
|---|---|---|
| EP | 0 292 220 | 11/1988 |
| EP | 0 661 028 | 7/1998 |
| WO | WO 87/02576 | 5/1987 |
| WO | WO 92/10168 | 6/1992 |
| WO | WO 93/02663 | 2/1993 |
| WO | WO 94/12150 | 6/1994 |
| WO | WO 95/15149 | 6/1995 |
| WO | WO 96/14326 | 5/1996 |

OTHER PUBLICATIONS

M. Larmas et al., Acta Odontologica Scandinavica, vol. 33, Suppl. 70, 1972: 45–55.

S.L. Vargas et al., "Modulating Effect of Dietary Carbohydrate Supplementation on Candida albicans Colonization and Invasion in a Neutropenic Mouse Model", Infect Immun. (1993); 61(2) : 619–626.

M. Uhari et al., "Xylitol chewing gum in prevention of acute otitis media: double blind randomised trial", BMJ, vol. 313 (1996): 1180–1184.

Albert Bar, "Fermentability of Xylitol and Other Sugar Substitutes", Caries Prevention with Xylitol: A Review of a Scientific Evidence, (1983): 55 Wld. Rev. Nutr. Diet: 183–209.

M. Larmas et al., Acta Odontologica Scandinavica, vol. 32, 1972, pp. 423–433.

Article entitled "Xylitol: An Update, Oral Health", vol. 71, 1981, No. 8, pp. 43–47.

* cited by examiner

*Primary Examiner*—Kevin E. Weddington
(74) *Attorney, Agent, or Firm*—Scully, Scott, Murphy & Presser

(57) ABSTRACT

The invention relates to the use of polyols such as xylitol for the preparation of a composition to be administered in the treatment or prophylaxis of mucosal yeast infection in mammals, as well as to preparations for use in the systemic or topical therapeutic or prophylactic treatment of mucosal yeast infections. The invention relates specifically but not solely to the combating of infections caused by Candida s.p. in mucosa in connection with exocrine glands of the mammalian body.

20 Claims, 2 Drawing Sheets

USE OF POLYOLS IN COMBATING YEAST INFECTION AND POLYOL PREPARATIONS FOR SAID USE

Figure 1:
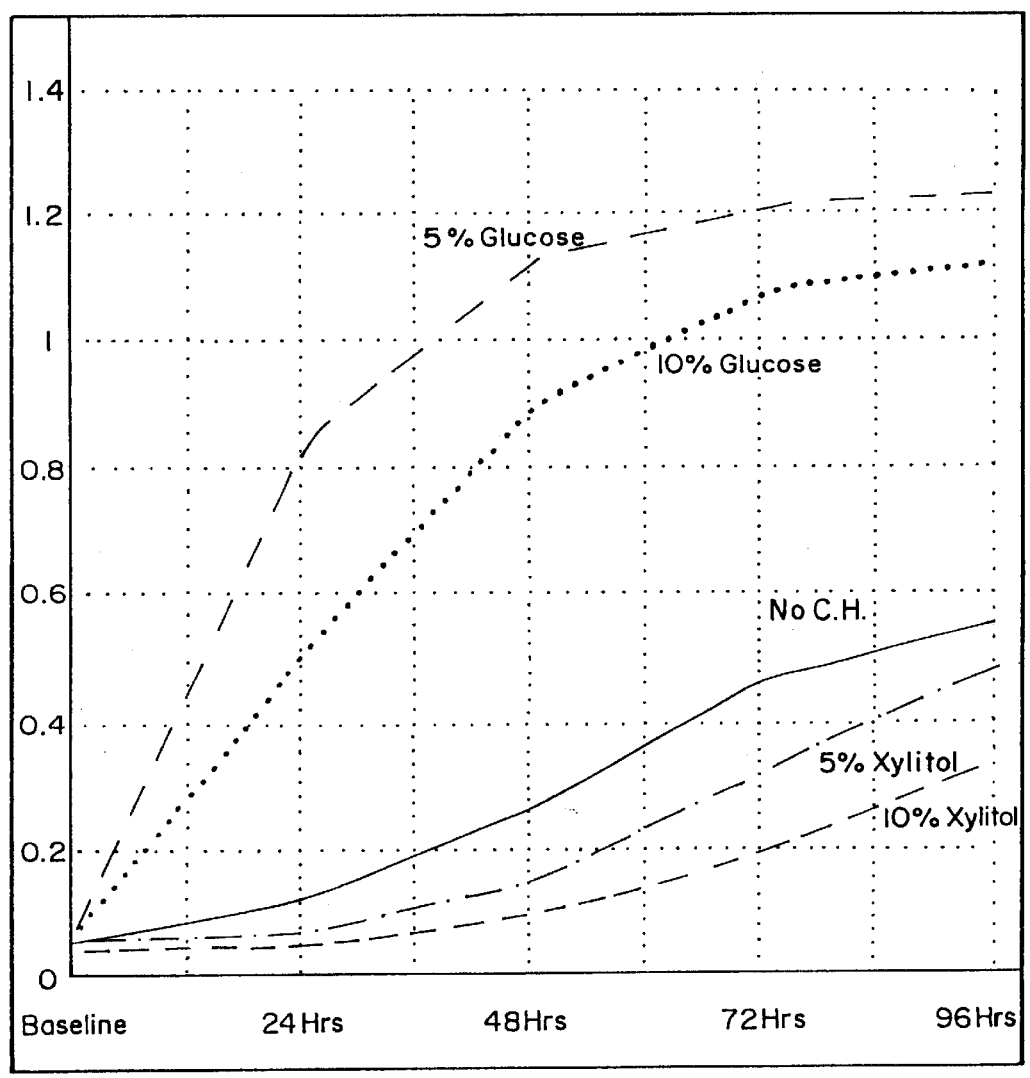

The present invention relates to the use of polyols such as xylitol for the preparation of a composition to be administered in the treatment or prophylaxis of mucosal yeast infection in mammals, as well as to preparations for use in the systemic or topical therapeutic or prophylactic treatment of mucosal yeast infections. The invention relates specifically but not solely to the combating of infections caused by Candida s.p. in mucosa in connection with exocrine glands of the mammalian body.

Despite the availability of effective antifungal drugs, optimal prophylactic and therapeutic approaches for mucositis are still controversial. Factors that might have a stimulatory effect on fungal growth or decrease the effectiveness of antifungal therapy of mucositis have received little attention.

Oral candidiasis is the most common opportunistic infection in AIDS, affecting up to 90% of the patients. It importantly interferes with nutrition. Studies suggest that the presence of oral candidiasis increases progression to AIDS, and that oral candidiasis is an independent risk factor for the development of *Pneumocystis carinii* pneumonia. Oral candidiasis is also one of the most common reasons for premature cessation of chemotherapy in cancer patients.

Optimal prophylaxis and therapy of oral candidiasis are still controversial issues. Oral nystatin and amphotericin B are usually effective, but compliance is problematic due to the unpalatable taste and gastric intolerance of these compounds. Drugs based on azoles are also effective, but resistance is an increasingly recognized problem. Recurrences are common. These issues warrant the search for novel strategies to prevent or treat candidiasis.

It is known that sucrose favours the growth of Candida in vitro and sucrose rinses have been thought to induce the development of oral candidiasis in some patients with dentures. Sucrose also increases gastrointestinal growth and mucosal invasion of *Candida albicans* in murine models.

Sucrose is the most commonly used sweetener for food and pharmaceutical contexts. Although a wide variety of alternate sweeteners are available, sucrose is generally considered to be the optimum sweetener with regard to taste profile and technological properties However, sucrose has been implicated as a contributory factor in many diseases including hypertension. coronary heart disease, arterial sclerosis and dental caries.

Perhaps the most significant, well-documented effect of sucrose is its contribution to tooth decay. The mouth contains a number of bacterial strains which ferment common dietary carbohydrates such as sucrose. This fermentation generates acid as an end product which lowers the pH in the mouth; the lowered pH leads to a demineralization of tooth enamel and finally to the formation of dental lesions of caries.

One approach to fighting dental caries is to reduce or eliminate the amount of fermentable carbohydrates such as sucrose in pharmaceutical or food contexts. The replacement of fermentable carbohydrates by sugar substitutes which cannot be fermented, or are less easily fermented by *S. mutans* and other bacteria has been shown to decrease the development of dental caries.

Xylitol is a naturally occurring five carbon sugar alcohol which has the same sweetness as sugar and a caloric content which is less than that of sugar. Xylitol is found in small amounts in many fruits and vegetables and is produced in the human body during normal metabolism. Xylitol is attractive as a sugar substitute in food contexts because of its known metabolic, dental and technical characteristics.

Xylitol has been used as a sugar substitute in certain contexts, such as chewing gum [U.S. Pat. No. 4,514,422 (Yang) and 3,422,184 (Patel)] with practical and commercial success. Xylitol has also been used in tablets [WO 92/10168 (Xyrofin Oy)], in sweets and chocolate, etc.

From a metabolic perspective, xylitol is metabolized largely independent of insulin, so it can be safely consumed by non-insulin dependent diabetics. A significant advantage of xylitol is that it is not fermented by *S. mutans* and other bacteria found in the mouth and, therefore, does not produce acids which, as described above, contribute to the formation of dental caries. Xylitol is well established as a non-cariogenic substance, i.e. xylitol does not contribute to caries formation. Significant data also exists which supports the view that xylitol is not only non-cariogenic, but actively suppresses the formation of new caries and may even reverse existing lesions by inducing remineralization, i.e. it is a cariostatic material.

A summary of clinical data regarding the effects of xylitol and its possible mechanisms is set forth in Bar, Albert, *Caries Prevention With Xylitol: A Review of a Scientific Evidence*, 55 Wld. Rev. Nutr. Diet. 183–209 (1983). The mechanism or mechanisms by which xylitol effects any cariostatic properties is not yet known, but some possible mechanisms which have been suggested include a reduction of oral levels of *S. mutans*, a reduction in the development of plaque, the stimulation of the flow of protective saliva, the favorable alteration of the composition of saliva, the retardation of demineralization and a enhancement of remineralization of tooth enamel.

Other polyols, such as sorbitol, mannitol and lactitol have also been substituted for sucrose in a variety of contexts. All of these polyols have certain advantages, such as non-cario-genicity, over sucrose. However, none of the other polyols have been demonstrated to have a cariostatic effect. Xylitol is also known to have a better patient compliance than other polyols.

In a study examining the oral microflora in relation to caries, it was found (M. Larmas, et al., Acta Odontologica Scandinavia, Vol. 33, Suppl. 70, 1975, p. 45–55) that substituting xylitol for sucrose in the diet of a human test group during 8 months significantly reduced the number of persons with salivary Candida growth, while there was a slight increase in the test groups receiving sucrose and fructose. At the base line practically every second person had Candida in the saliva.

Xylitol has been documented [S. L. Vargas et al., Infect. Immun. 1993; 61(2):619–26] as a potential candidate for replacing glucose in an immunocompromised murine model of gastrointestinal candidiasis, as it did not increase Candida growth nor invasion compared to controls when given instead of glucose. Mice receiving xylitol had five times less invasion of gastrointestinal mucosa by Candida, than did mice receiving glucose. Xylitol scores of invasion were not significantly different from those of the control mice receiving no sugar.

A two month regular use of xylitol chewing gum has been shown to reduce the occurrence of acute otitis media in children [M. Uhari, et al., BMJ, Vol. 313 (1996); 1180–1184]. The effect was attributed to the efficacy of xylitol in reducing the growth of *S. pneumoniae* and thus preventing the attacks of acute otitis media caused by pneumococci.

The occurrence of mucositis and especially oral candidiasis in AIDS patients is an increasing problem in the world.

Antifungal therapies have not proven successful in all cases and fungal resistance to the available drugs is a frequent problem. Oral candidiasis is very painful and provides the patients with a poor quality of life. There is felt to be a real need for improving the available therapies for mucositis.

Despite the fact that the beneficial effect of replacing sucrose with xylitol in combating dental caries has been known for a long time and although xylitol was found not to increase gastrointestinal candidiasis as much as sucrose, no suggestion has been made for utilizing xylitol or other polyols for combating mucositis caused by yeasts on mucosa in close connection with exocrine glands of the body.

The present inventors have now surprisingly found that a polyol such as xylitol has a marked beneficial effect in preventing yeast growth on mucosa at various orifices of the body and that said polyol consequently is useful in the treatment and prevention of mucositis in such areas in mammals. A polyol according to the present invention indicates a polyol such as xylitol, lactitol, mannitol, sorbitol or mixtures thereof. Xylitol is the preferred polyol. Thus, when the present specification mentions xylitol as the polyol, this is indication of the preferred embodiment, but it should be observed that said mention is intended to cover also the other polyols which function in the same way. However, the inventors have found that the effect of xylitol is significantly better than that of other known polyols such as sorbitol and lactitol. Its effect seems not to be contributable only to a reduction in the amount of fermentable carbohydrates. Xylitol has been found to improve the conventional antifungal therapies when administered in combination with such drugs.

The present invention accordingly provides a new use of a polyol such as xylitol in the preparation of a composition to be administered in the treatment or prophylaxis of mucosal yeast infection in mammals. According to the invention at least one pharmacologically acceptable carrier is mixed with an amount of xylitol sufficient to reduce or inhibit mucosal infection caused by yeasts such as Candida s.p. in said mammal.

The invention offers a method for improving the therapeutic and/or prophylactic treatment of mammals suffering from or being subject to an increased risk of mucosal yeast infection, said method comprising administering a polyol such as xylitol to said mammal in an amount which is effective in reducing or inhibiting mucosal infections caused by yeasts such as Candida s.p in said mammal. The therapeutic treatment may favorably include a simultaneous administration of antifungal drugs. Generally the antifungal drug is administered at a dose level below the level given when not in combination with xylitol.

Thus, a synergistic effect can be observed when xylitol is administered in combination with conventional antifungal drugs.

According to the invention xylitol may be incorporated into a composition or a pharmaceutical preparation for use in the systemic or topical therapeutic or prophylactic treatment of mucosal yeast infections in mammals. Such a composition or preparation contains at least one pharmacologically acceptable carrier and an amount of xylitol sufficient to reduce or inhibit mucosal infection caused by yeasts, such as Candida s.p. in said mammal, or sufficient to enhance the effect of other antifungal drugs used in the treatment of said infection.

In a preferred embodiment of the invention the mucosal infection to be treated is caused by a Candida s.p. yeast such as *Candida albicans*, especially in mucosa in connection with exocrine glands of the body of the mammal. Another genus of opportunistic yeasts which may cause infections are Torulopsis s.p., especially *Torulopsis glabrata*. Both *Candida albicans* and *Torulopsis glabrata* are part of the normal flora of the mouth and vagina or urinary tracts of mammals. However, under favourable conditions they cause infections of the mucosa.

It is to be noted that although the mammal in question may be selected from the group comprising human beings, mammalian pet animals such as cats and dogs, mammalian farm animals such as horses, cattle, pigs, and the like, the greatest problems are generally observed with human beings who suffer from reduced immune defense such as AIDS patients.

AIDS patients are especially prone to suffer from oral yeast infections, especially oral candidiasis or thrush, which causes great pain at all times and especially in connection with food intake.

Mucosal infections in connection with exocrine glands may, however, occur also as mastitis, vaginal infection, as infections of the urinary tracts or even in the eyes. Animals may also suffer from yeast infections on mucosa and an example is udder infection or mastitis in milking cows.

In the practice of the present invention, the polyol such as xylitol is incorporated into a pharmaceutical composition to be administered via systemic or topical administration. Xylitol may be used alone or in combination with various antifungal drugs effective in the combating of the mucositis. In some cases the effective drug has a unpleasant taste, in which case a physical combination of xylitol with the drug has the dual effect of providing xylitol to the patient and masking the bad taste of the drug. A combination of polyols may also be used.

Among the antifungal drugs used in the treatment of oral mucositis, drugs such as nystatin, amfotericin B, and various azoles may be mentioned. In the therapy of oral candidiasis where xylitol alone is not considered sufficient, it is preferred to use nystatin in combination with the xylitol at least until the lesions are cured.

It is preferred to provide the xylitol to be used for the prevention or inhibition of mucositis in the form of an orally administrable preparation. Such a preparation may be in the form of a liquid, a tablet, a pill, a lozenge, a chewing gum or tablet, a powder, a spray, a syrup, a sugar substitute, a candy or sweet, an ice-cream, a pet food, an animal feed, and the like. The preparation may be produced by mixing at least one pharmacologically acceptable carrier and an amount of xylitol sufficient to reduce or inhibit the infectious activity of yeasts on the mucosa.

The amount of polyol included in any specific preparation of course depends on how much of the preparation in question that would be taken per day by the patient. The dose should be high enough to provide a significant effect on the yeast infection but not too high to cause the mammal adverse reactions in the form of diarrhea or flatulence. On the other hand, the effect of xylitol has been found to be dose dependent in the sense that an increased level of xylitol causes a more marked reduction of yeast growth.

A suitable amount of xylitol in a preparation may be calculated so as to give the mammal a daily oral xylitol dose of about 0.05 to 1.0 g xylitol per kg of body weight, preferably 0.1 to 0.8 g/kg and most preferably about 0.2 to 0.5 g/kg. Higher amounts of xylitol may be given for shorter periods, but it should be noted that high doses of xylitol may have adverse effects on some patients, most notably in the form of diarrhea.

One easy way of providing for a suitable oral intake of polyol is to administer the polyol as a sugar substitute in the diet of the patient.

In connection with oral mucosal infections the oral administration is at the same time a topical administration. The polyol may also be applied locally to other infection areas. Such topically administrable preparations may be in the form of a liquid, a spray, an aerosol, a cream, a paste, a cement, an ointment, a jelly or gel, a lubricant, a plaster, a membrane, a mouth wash or rinse, a tooth paste, eye drops, etc. They may be prepared, for instance, by mixing at least one topical carrier and an amount of xylitol sufficient to reduce or inhibit the infectious activity of yeasts on the mucosa.

For the specific use of xylitol in combating vaginal infection, the specific topical composition should be in a form suitable for vaginal use. The xylitol may thus be included in a cream, jelly, lubricant, or liquid or it may preferably be applied onto the surface of a condom.

In present times it has become popular to provide condoms with various flavors, such as strawberry or banana. Correspondingly, the polyol such as xylitol may be added to condoms as an antifungal humectant and sweetener compound. Thus, the condom embodiment of the invention provides an easy way of providing xylitol to infected or potentially infectious mucosa at orifices of the human body, such as the vagina.

For the specific use of the polyol in combating udder infection in cows, the topical composition should preferably be in a form suitable for being easily applied on a farm. Xylitol is preferably included in a liquid spray or a dip. The xylitol may, however, also be included in a moist tissue.

For oral intake by pet animals, cattle, etc. the xylitol may be included in a xylitol containing food or feed additive. The additive may contain other polyols but it preferably should not contain glucose. The amount of xylitol in the additive should be more than 10% and it should preferably be over 30%, most preferably over 40% of the total polyol content of the additive. The most preferred additive would be one wherein 50 to 100% of said polyol is xylitol. Such a product might, however, be too expensive for normal use and it is therefore suggested to mix the xylitol with other components such as non-toxic, non-carbohydrate excipients.

The polyol may also be mixed directly into pet food or animal feed preparations in an amount to provide a daily dose of about 0.05 to 1,0 g xylitol per kg of body weight, preferably 0.1 to 0.8 g/kg and most preferably about 0.2 to 0.5 g/kg.

The invention will now be illustrated further with the aid of a few examples. It should be noted that these examples are not to be construed as limiting the invention in any way.

EXAMPLE 1

A pilot study was designed to test the effect of xylitol on the clinical course, Candida salivary counts, and antifungal needs of patients with recurrent oral candidiasis. The patients were instructed to replace their dietary saccharose with crystalline xylitol and to avoid excess saccharose-containing-foods and beverages.

Of 14 patients admitted to the test, 8 completed more than 14 days of follow up. The result was that all 8/8 experienced at least 70% regression of their lesions (improvement) with minimal antifungal therapy (1 nystatin tablet 500,000 U/per day); 5/8 had complete regression of the lesions (cure); and 6/8 decreased their salivary Candida counts by 2 logs.

Three patients returned to baseline 3 days after returning to saccharose intake. 1 patient completed 4 months of xylitol intake without lesions and sterile fungal cultures, having had a previously identified fluconazole resistant isolate (E test).

The results show that oral administration of xylitol instead of dietary saccharose affected the pathogenesis of oral candidiasis and in some patients improved the efficacy of antifungal therapies.

EXAMPLE 2

An open label, pilot trial was designed to test the effect of the strategy of dietary xylitol intake in replacement of sugar in patients with candida mucositis. AIDS patients with oral or esophageal candidiasis were selected as subjects for the study because of the frequency and the severity of candida mucositis that they usually develop.

Patients with AIDS were considered eligible for the test after their oral or esophageal lesions were documented by microscopic examination of scrapings to be of Candida origin. They were free to continue on any antifungal therapy they might be receiving.

Instructions were given to replace the saccharose that they normally take with coffee or tea for crystalline xylitol. Also, to avoid excess sweets like ice cream, cakes. cookies, and artificially flavored drinks that contain glucose.

The following was done at baseline and thereafter every 7 days:
1. Pictures of the lesions
2. Tongue imprints in Sabouraud agar
3. Quantitative Candida cultures on unstimulated saliva (CFU/ml)
4. Pain questionnaire (numerical pain scale)
5. Weight
6. Patients kept a daily record of food and drink.

AIDS patient No. 1 had suffered from oral candidiasis for about 9 months with episodes of oral candidiasis recurring with almost no symptom-free periods. The patient received AZT as antiretroviral therapy and ketoconazole as antifungal therapy.

The patient noticed clear improvement on day four of the trial and voluntarily discontinued ketoconazole at this point. The lesions continued to improve and disappeared after 1 week in the trial. The Candida counts that were $1 \times 10^4$ on day one, became negative at day seven, and were still negative after 2.5 months.

The patient completed a symptom-free, follow-up period of 80 days, and gained 13.1 kilograms weight (From 62 to 75.1 kg) The daily xylitol intake was approximately 6–8 sugar spoons (about 30 g) of crystalline xylitol. The results are shown below in Table 1.

TABLE 1

| Day | 1 | 8 | 18 | 29 | 36 | 56 | 80 |
|---|---|---|---|---|---|---|---|
| CFU/mL saliva | $1 \times 10^{4*}$ | 0** | 0** | 0** | 0** | 0** | 0** |
| Sympt. score | 18 | 0 | 0 | 0 | 0 | 0 | 0 |
| Weight (Kg) | 62 | 62.6 | 73.4 | 73 | 74.8 | 75 | 75.1 |

*counted at 48 hours
**plates held for 7 days before calling them sterile

AIDS patient No 2 was diagnosed to have Candida esophagitis but was receiving no antifungal therapy. Two weeks after the start of xylitol intake the patient had unchanged lesions and was started on fluconazole p.o. for a 15 days period. Follow up esophagoscopy done a month later revealed no lesions. The results are shown below in Table 2.

TABLE 2

| Day | 1 | 7 | 15 | 22 | 29 | 36 | 50 |
|---|---|---|---|---|---|---|---|
| CFU/ml saliva | $6 \times 10^{2}$* | 0 | $3,6 \times 10^{3}$** | $4,5 \times 10^{2}$** | 0 | 0 | 0 |
| Sympt. score | 18 | 0 | 0 | 0 | 0 | 0 | 0 |
| Weight (Kg) | 58,5 | 58,5 | 58,5 | 57,5 | 57,2 | 57,7 | 56,9 |

*counted at 48 hours
**counted at 72 hours (unable to count at 48 hours, as colonies were too small)

AIDS patient No. 3 had recurrent oral candidiasis for nearly two years with multiple recurrences and almost no symptom-free periods. There was no longer any response to antifungal multiple therapies with azoles. The oral mucosa was totally covered with white plaques. There was considerable pain.

The patient kept taking 1 nystatin troche during the first five days of the xylitol trial. The pain symptoms were reduced from 30 to 8 in the first 17 days and the saliva counts diminished. However, the patient then got another illness and retired from the trial.

The oral candidiasis recurred 4 days after stopping the xylitol trial.

EXAMPLE 3

Candida isolate from AIDS patient No 1 of Example 2 was tested for sensitivity and was found to be resistant to Fluconazole (MIC>256 µg/ml) and sensitive to Amphotericin B.

The effect of sugar alcohols on the growth of said Candida isolate was tested on Muller Hinton agar with 5 and 10% glucose or 5 and 10% xylitol and a control without sugar. The growth was found to be inhibited in a dose dependent way by xylitol when compared to the controls (FIG. 1). Glucose increased the growth quite considerably.

EXAMPLE 4

A test was designed to determine the effect on the growth in vitro of *Candida albicans* of xylitol, lactitol, sorbitol and aspartame in comparison to glucose and a non-carbohydrate control medium. The tested substances have all been used in the food industry as sweeteners. The sweetness of the substances in the above order is respectively 100%, 40%, 60% and 20.000% of the sweetness of glucose.

12 strains of *Candida albicans* obtained from patients with AIDS and oral candida mucositis were evaluated. The strains were inoculated on Sabouraud agar plates (20% dextrose) and incubated at room temperature for 48 hours. One colony from each plate was inoculated in Muller Hinton broth (without sweetener) and left for 18 hours at 35° C. The tubes were standardized to Mac Farland 0.5 ($5 \times 10^6$ CFU/ml) and 100 µl inoculated in triplicate in spectrophotometer tubes containing 3 ml of Muller Hinton broth at final concentrations of glucose (5% and 10%); xylitol (5% and 10%); lactitol (5%, 8.3% and 10%); sorbitol (5%, 10% and 12.5%); and aspartame (0.025% and 0.05%). 3 tubes with Muller Hinton broth without carbohydrate was also inoculated to serve as controls.

Figure 2:
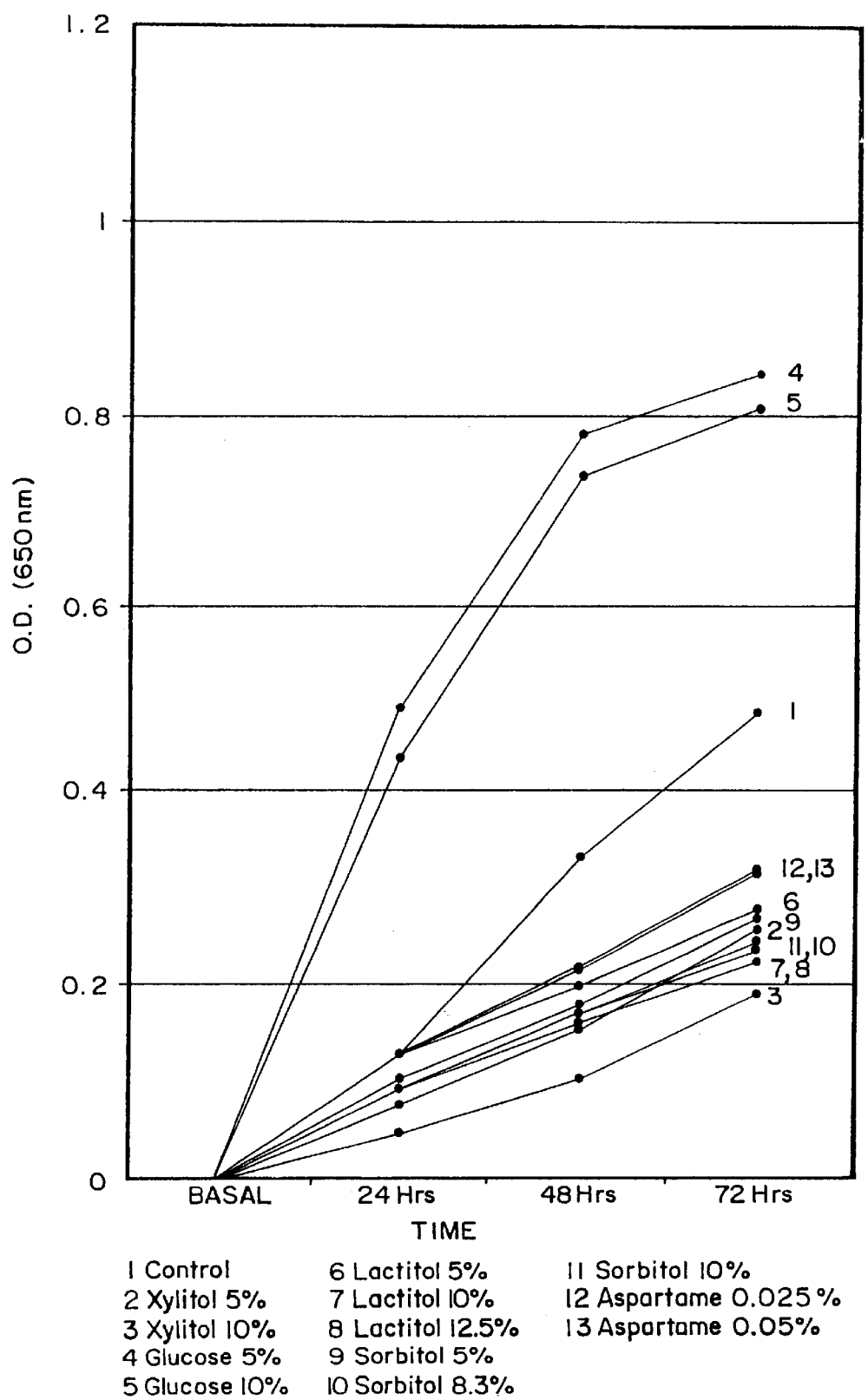

Optical densities (650 nm) were determined at 0, 24 and 48 hours time. The average of three readings per time, per sweetener concentration was calculated and recorded. The results of the test are indicated in FIG. 2 showing the summary curve of the averages of all the strains in each of the test mediums.

The results clearly indicate that glucose has an effect of increasing the growth of Candida in comparison to the control without carbohydrate. The artificial sweeteners all reduced the growth of Candida compared to the control. Xylitol at 10% concentration proved to be by far the best of the tested compounds at reducing the growth of Candida in vitro.

What is claimed is:

1. A method for the therapeutic or prophylactic treatment of mammals suffering from or being subject to an increased risk of mucosal yeast infection, said method comprising administering to said mammal, a polyol in an amount which is effective in reducing or inhibiting mucosal infection caused by yeast in said mammal, or effective in enhancing the effect of other antifungal drugs used in the treatment of said infection.

2. The method according to claim 1 wherein the polyol is the sole active agent in the treatment or prophylaxis of mucosal infection.

3. The method according to claims 1 or 2 wherein the polyol is selected from the group consisting of xylitol, lactitol, sorbitol, mannitol and mixtures thereof.

4. The method according to claims 1 or 2 wherein said yeast is a Candida s.p.

5. The method according to claims 1 or 2 wherein said mucosal infection is an infection of the mucosa in connection with exocrine glands of the body of said mammal.

6. The method according to claims 1 or 2 wherein said mammal is selected from the group consisting of human beings, mammalian pet animals, and mammalian farm animals.

7. The method according to claim 6, wherein said mammal is a human being suffering from AIDS.

8. The method according to claims 1 or 2 wherein said polyol is administered by systemic or topical administration.

9. The method according to claim 8, wherein xylitol is administered orally.

10. The method according to claims 1 or 2 wherein xylitol is administered as a sugar substitute in the diet of said mammal.

11. The method according to claim 10, wherein said mucosal yeast infection is an oral infection, especially oral candidiasis.

12. The method according to claims 1 or 2 wherein said mucosal yeast infection is a vaginal infection.

13. The method according to claims 1 or 2 wherein said mucosal yeast infection is mastitis or an udder infection.

14. A composition for use in the therapeutic or prophylactic treatment of mammals suffering from or being subject to an increased risk of mucosal yeast infections, containing at least one pharmacologically acceptable carrier and an amount of polyol sufficient to reduce or inhibit mucosal infection caused by yeast in said mammal.

15. The composition according to claim 14 wherein the polyol is the sole active agent in the treatment or prophylaxis of mucosal infection and the polyol is selected from the group consisting of xylitol, lactitol, sorbitol, mannitol and mixtures thereof.

16. The method according to claim 6, wherein said Candida s.p. is *Candida albicans*.

17. The composition according to claim 14, wherein said yeast is Candida s.p.

18. The composition according to claim 17, wherein said Candida s.p. is *Candida albicans*.

19. The method according to claim 3, wherein said polyol is xylitol.

20. The composition according to claim 3, wherein said polyol is xylitol.

* * * * *